United States Patent
Marfat et al.

Patent Number: 6,043,379
Date of Patent: Mar. 28, 2000

[54] PROCESSES AND INTERMEDIATES FOR PREPARING 2-FLUOROTHIOPHENE DERIVATIVES

[75] Inventors: Anthony Marfat; Robert James Chambers, both of Mystic, Conn.

[73] Assignee: Pfizer Inc., New York, N.Y.

[21] Appl. No.: 09/355,265

[22] PCT Filed: Mar. 9, 1998

[86] PCT No.: PCT/IB98/00304

§ 371 Date: Jul. 26, 1999

§ 102(e) Date: Jul. 26, 1999

[87] PCT Pub. No.: WO98/45282

PCT Pub. Date: Oct. 15, 1998

Related U.S. Application Data

[60] Provisional application No. 60/043,901, Apr. 4, 1997.

[51] Int. Cl.[7] .................................................. C07D 333/38
[52] U.S. Cl. .............................................................. 549/71
[58] Field of Search .................................. 549/71, 72, 73

[56] References Cited

U.S. PATENT DOCUMENTS 5,047,554  9/1991  Ehrgott et al. ........................... 548/486

OTHER PUBLICATIONS

Gronowitz, S.—Chem. Abst.—vol. 75, No. 3, Jul. 19, 1971, Abst No. 20080c, Nuclear Magnetic Resonance of aromatic heterocyclics. III On the synthesis of substituted fluorothiophenes.
Gronowitz, S.—Chem.Scripta, vol. 1., pp. 33–43, 19/1, Nuclear Magnetic Resonance of aromatic heterocyclics. III On the synthesis of substituted fluorothiophenes.
Suzuki, H.—Chem. Soc. Japan, Bull Chem Soc. Jpn. vol 63., No. 7, pp. 2010–2017, (1990) General & Highly Eff. Syntheses of m–Fluoro Arenes Using Potassium Fluorido Exchange Method.
Yazawa. N.—Chem. Letters (1980) pp2213–2216, Chem Soc. Of Japan—Tetraphenylphosphonium Bromide Catalyzed . . . Compound.
Heinz, P.—Chem. Abst., vol. 80, p. 663—Abst. No. 163322h—Nov. 6, 1978—Some thieny analogs of amidinomycin.
Dann, O.—Chem. Abst. vol. 37, No. 21—Col. 6260, Nov. 10, 1943—Aminocarboxylic ester of furan. thiophene & thiazole.
CA 115: 471386 Preparation of . . . biosynthesis. Ehrgott et al., Sep. 1999.
CA 98: 16219 Protonation of . . . –carboxamides. Alberghina et al., 1983.

Primary Examiner—Deborah C. Lambkin
Attorney, Agent, or Firm—Peter C. Richardson; Paul H. Ginsburg; Jolene W. Appleman

[57] ABSTRACT

A process for the preparation of the compound of the formula

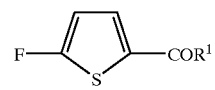

I wherein $R^1$ is OH, which comprises the steps of a) treating the compound of the formula

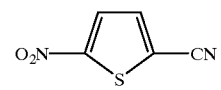

III with an inorganic fluoride, of the formula $M^2F$ wherein $M^2$ is an alkali metal cation, at an elevated temperature in the presence of a compound of the formula $R^4P^+Z^-$ and a compound of the formula $R^5vic\,(COW)_2$ wherein $R^4$ and $R^5$ are each selected from optionally substituted $(C_6–C_{10})$aryl and optionally substituted $(C_1–C_6)$alkyl, and W is halo; to form the compound of the formula;

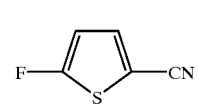

IV and b)
i) treating the compound of the formula IV with an aqueous solution of a base, of the formula MOH, wherein M is an alkali metal cation, and
ii) treating the product of step i) with a mineral acid. A compound of the formula

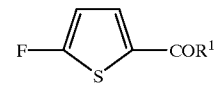

wherein $R^1$ is selected from the group consisting of, halo, $R^7O$, $R^7COO$ and $N(R^8)_2$ wherein $R^7$ is $(C_1–C_6)$alkyl or $(C_6–C_{10})$aryl and each $R^8$ is selected from hydrogen and $R^7$ with the proviso that $R^7$ is not methyl when $R^1$ is $R^7O$.

10 Claims, No Drawings

PROCESSES AND INTERMEDIATES FOR PREPARING 2-FLUOROTHIOPHENE DERIVATIVES

Provisional Application No. 60/043,901 Apr. 4, 1997. This application is a 371 of PCT/IB98/00,304 Mar. 9, 1998.

BACKGROUND OF THE INVENTION

This invention relates to processes and intermediates for preparing 3-substituted-2-oxindoles of the formula II below. 5-Fluorothiophen-2-ylcarboxylic acid, and its derivatives, of the general formula (I), below, are useful in the preparation of compounds of the formula II wherein n is 0 and Q is

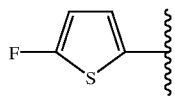

Compounds II, their pharmaceutically acceptable salts and prodrugs (hereafter "the active compounds") are useful as inhibitors of prostaglandin $H_2$ synthase, 5-lipoxygenase and interleukin-1 biosynthesis. They are also useful as analgesic, antiinflammatory and antiarthritic agents in the treatment of chronic inflammatory diseases.

U.S. Pat. No. 5,290,802 (hereafter "the 802 patent"), assigned to the Assignee of this application and incorporated herein in its entirety, discloses compounds of the formula

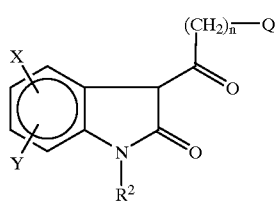

wherein Q, X, Y, n and $R^2$ are defined therein, their preparation from compounds of the formula Q—$(CH)_2CO_2H$, and methods for preparing compounds of the formula Q—$(CH)_2$ $CO_2H$, wherein Q is defined therein.

Gronowitz, S. and Rosen, U, (*Chemica Scripta* 1971, 1, 33–43) describe a preparation of I starting from lithiated compounds.

SUMMARY OF THE INVENTION

According to a first embodiment of the invention there is provided a method for preparing a compound of the formula

I

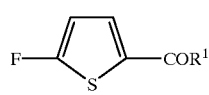

wherein $R^1$ is OH, which comprises treating the compound of formula

III

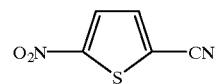

with a metallic fluoride ($M^2$ F), wherein $M^2$ is an alkali metal cation wherein the metal is, preferably, selected from K'Cs and Rb, at a high temperature, in an inert solvent. The reaction is effected in the presence of a mixture of compounds of the formulae $(R^4)_4P^+Z^-$ and $R^5vic(COW)_2$, wherein "vic" indicates that the "COW" groups are attached to adjacent ("vicinal") C atoms on the $R^5$ group; and $R^4$ is selected from optionally substituted $(C_1-C_6)$alkyl and optionally substituted $(C_6-C_{10})$aryl, such as n-butyl and phenyl, respectively, and Z is selected from Br and Cl, $R^5$ is $(C_6-C_{10})$aryl, such as phenyl or naphthyl, or $(C_1-C_6)$alkyl, such as butyl, and W is selected from Cl and F, to form the compound of the formula

IV

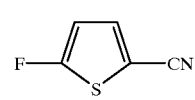

Compound IV is then heated with an aqueous solution of MOH, wherein M is an alkali metal, preferably selected from Li, Na and K, and the resultant product is treated with a mineral acid, preferably selected from HCl, $H_2SO_4$ and $H_3PO_4$, to form the compound of formula I wherein $R^1$ is OH.

Another aspect of the above embodiment provides a method for preparing a compound of formula I, wherein $R^1$ is a halogen atom, by treating the corresponding compound of formula I wherein $R^1$ is OH with a halogenating agent.

Yet another aspect provides a method for preparing a compound of formula I, wherein $R^1$ is selected from amino, mono$(C_1-C_6)$alkylamino, di$(C_1-C_6)$alkylamino, $(C_6-C_{10})$ aroyloxy, $(C_1-C_6)$acyloxy, $(C_6-C_{10})$aryloxy, and $(C_1-C_6)$ alkoxy, which comprises treating the corresponding compound wherein $R^1$ is a halogen atom with an appropriate amine; aromatic or alkyl carboxylic acid or salt thereof; phenol or alkanol.

Another embodiment of the invention provides a compound of formula I wherein $R^1$ is an amino, mono$(C_1-C_6)$ alkylamino, di$(C_1-C_6)$alkylamino, $(C_6-C_{10})$aroyloxy, $(C_1-C_6)$acyloxy, $(C_6-C_{10})$aryloxy, or $(C_2-C_6)$alkoxy group.

DETAILED DESCRIPTION OF THE INVENTION

In the Schemes and the following discussion $M^2$, X, Y, Z, W, $R^{1-}$, $R^4$ and $R^5$ and formulae I, II, III and IV have the meanings given above.

SCHEME 1

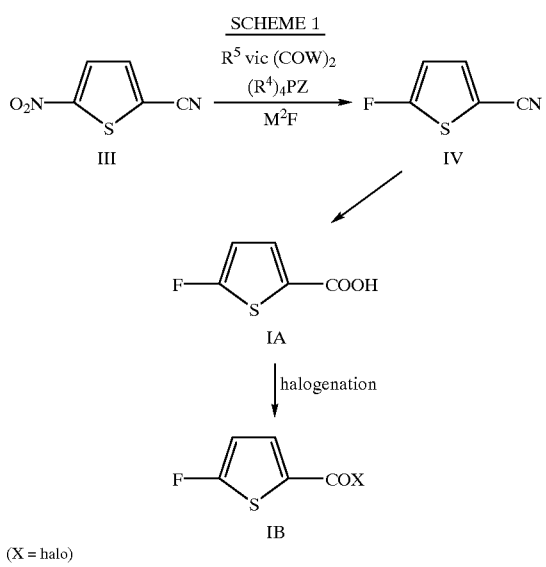

(X = halo)

As shown in Scheme 1 compound III is converted to compound IV by treatment with a fluoride of the formula $M^2F$ wherein $M^2$ is an alkali metal cation, preferably selected from K, Cs and Rb, in an inert solvent at a temperature from about 140 to about 220° C. The reaction is effected in the presence of a mixture of the compounds of the formulae $(R^4)_4P^+Z^-$ and $R^5vic(COW)_2$ wherein $R^4$ is a $(C_6-C_{10})$aryl or $(C_1-C_6)$alkyl group such as phenyl and n-butyl, espectively, and $R^5$ is $(C_6-C_{10})$aryl, such as phenyl or naphthyl, or $(C_1-C_6)$alkyl, such as butyl, disubstituted with COW groups on adjacent carbon atoms wherein W is any halo group, preferably Cl and F. Inert solvents useful in this step are aprotic polar solvents such as disubstituted cyclic and acyclic sulfones, sulfoxides, amides and ureas having boiling points equal to or greater than 140° C. including Sulfolane, dimethylsulfoxide (DMSO), dimethylformamide (DMF) and 1-methyl-2-pyrrolidone (NMP). Preferably the reaction is carried out using KF in Sulfolane, (trademark) at about 180° C., in the presence of $(C_6H_5)_4PBr$ and 1,2-phenyl$(COCl)_2$.

Compound IV is then hydrolyzed, in an inert polar solvent selected from cyclic ethers, such as THF and dioxane; N,N-dialkylsubstituted acylamides, such as DMF and dimethylacetamide (DMAC); and water, with a base, of the formula $M(OH)_n$ wherein M is any Group I or II metal and n is 1 or 2. The reaction is effected, preferably, when n is 1 and M is K, Na or Li, at a temperature from about 20 to about 100° C. and the solvent is water. The resulting product is treated with a mineral acid, such as HCl, $H_2SO_4$ and $H_3PO_4$ to form compound IA. Preferably, the hydrolysis is effected in a refluxing aqueous NaOH solution and the acidification is effected with HCl.

Compound IB is prepared by treating compound IA with any of the halogenating agents known to the art, such as thionyl chloride, phosphorous tri- and pentahalides and phosphorous oxyhalides, in an inert solvent selected from halogenated alkanes such as methylene chloride and chloroform; cyclic ethers, such as THF and dioxane; N,N-dialkylsubstituted acylamides, such as DMF and DMAC; and mixtures thereof, e.g., methylene chloride and DMF. The reaction is effected at a temperature from about 0 to about 100° C. Preferably, the reaction is effected using thionyl chloride in methylene chloride, at reflux, in the presence of a catalytic amount of DMF.

Compounds of the formula I, wherein $R^1$ is $R^7O$, can be prepared by the standard methods known in the art, by reacting compounds of formulae IA or IB with $R^7OH$, or a salt thereof, wherein $R^7$ is an optionally substituted $(C_1-C_6)$ alkyl or $(C_6-C_{10})$aryl group, in the presence of an acid scavenger. (See e.g., Haslam, E in Tetrahedron, 36, 2409–2433 [1980]) Compounds of the formula I, wherein $R^1$ is $R^7COO$ can be prepared, for example, by reacting a compound of the formulae IA or IB with a compound of the formula $R^7COOH$, or a salt thereof, wherein $R^7$ is as defined above, under conditions well known in the art. (See e.g., Gallagher, P. T. and Gilmore, J. in Compr. Org. Funct. Group Transform. (1995), Volume 5, 181–229 1161–1308, Elsevier, Oxford, UK) The compounds of formula I, wherein $R^1$ is $(R^8)_2N$ can be prepared by reacting a compound of the formulae IA or IB with a compound of the formula $(R^8)_2NH$, wherein each $R^8$ is independently selected from hydrogen and $R^7$ wherein $R^7$ is as defined above. (See, e.g., Bailey, P. D. et al., Ibid, 257–307).

The compounds of the formula I wherein $R^1$ is OH are acidic and form base salts. All such base salts are within the scope of this invention and they can be prepared by conventional methods, For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Typical salts of the compounds of formula I which can be prepared are primary, secondary and tertiary amine salts, alkali metal salts and alkaline earth metal salts. Especially valuable are the ethanolamine, diethanolamine and triethanolamine salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides such as sodium ethoxide and potassium methoxide; hydrides, such as calcium hydride and sodium hydride; and carbonates and bicarbonates, such as potassium carbonate and sodium carbonate.

The ability of the active compounds to inhibit interleukin-1 biosynthesis is demonstrated by the assay procedure described in the '802 patent.

The analgesic activity of the active compounds makes them useful for acute administration to mammals for the control of pain, e.g., post-operative pain and the pain of trauma. Additionally, the active compounds are useful for chronic administration to mammals for the alleviation of the symptoms of chronic diseases, such as the inflammation of rheumatoid arthritis and the pain associated with osteoarthritis and other musculoskeletal disorders.

The ability of the active compounds to inhibit IL-1 biosynthesis makes them useful IL-1 biosynthesis inhibitors, per se. It also makes them useful in treating IL-1 mediated disorders and immune dysfunctions in a mammal. Said IL-1 mediated disorders include, but are not limited to, bone and connective tissue metabolism disorders such as osteoporosis, periodontal disease and tissue scarring. IL-1 mediated immune dysfunctions include, but are not limited to, allergy and psoriasis.

The ability of the active compounds to inhibit prostaglandin $H_2$ synthase makes them useful as prostaglandin $H_2$ synthase inhibitors, per se, as the functioning of that enzyme is known to be involved with the pathogenesis of athritic joints in mammals.

When an active compound is to be used as an inhibitor of IL-1, an inhibitor of prostagiandin $H_2$ synthase, an analgesic agent or an antiinflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising an active compound the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use the active compound can be administered, for example, in the form of tablets or capsules, or as an aqueous solution or suspension. In the case of tablets for oral use, carriers which are commonly used include lactose and corn starch and lubricating agents, such as magnesium stearate. For oral administration in capsule form, useful diluents are lactose and dried corn starch. When aqueous suspensions are required for oral use the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared and the pH of the solutions is suitably adjusted and buffered. For intravenous use, the total concentration of solutes should be controlled to render the preparation isotonic.

When an active compound is used in a human subject, the daily dosage will normally be determined by the prescribing physican. Moreover, the dosage will vary according to the age, weight and response of the individual patient, as well as severity of the patient's symptoms and the potency of the particular compound being adminstered. However, for acute adminstration to relieve pain, an effective analgesic response eliciting dose, in most instances, will be about 5 mg to 500 mg as needed (e.g., every four to twenty-four hours). For chronic adminstration to alleviate (treat) (chronic) inflammation and pain, inhibit IL-1 biosyntheses and/or inhibit prostaglandin $H_2$ synthase, in most instances, an effective dose will be from about 5 mg to 1.0 g per day, and preferably 50 mg to 500 mg per day, in single or divided doses. On the other hand, it may be necessary to use dosages outside these limits in some cases.

The following Examples are illustrative of this invention and are not to be construed as limiting in any way the scope thereof.

EXAMPLE 1

5-Fluoro-thiophene-2-carbonitrile

A mixture of 5-nitro-thiophene-2-carbonitrile (5.0 g, 32 mmol.), potassium fluoride (9.4 g, 162 mmol), tetraphenylphosphonium bromide (1.25 g, 3 mmol) and phthaloyl dichloride (4.3 mL, 32 mmol) in Sulfolane (100 mL) was heated to 180° C. for 2 hours. The mixture was poured into water (500 mL) and extracted two times with 250 mL diethyl ether. The organic extracts were combined, washed with 1N NaOH (80 mL), two times with 80 mL water, brine (80 mL), dried ($MgSO_4$) and concentrated in vacuo to give an oil. Flash chromatography on silica gel eluting with diethyl ether:pentane (1:3) afforded an amber oil. Distillation yielded 2.4 g (63%) of the title product as a clear oil (bp 171–3° C./760 mm Hg). $^1$H-NMR ($CDCl_3$): δ 7.32 (m, 1H), 6.55 (m, 1H). GC-MS (m/e, %): 127 ($M^+$, 100).

EXAMPLE 2

5-Fluoro-thiophene-2-carboxylic acid

A mixture of the title product of Example 1 (1.5 g, 11.8 mmol) and 1.0 N NaOH (25 mL, 25 mmol) was refluxed for 3 hours. The mixture was poured into water (200 mL) and washed two times with 200 mL diethyl ether. The aqueous extract was acidified with 1N hydrochloric acid to pH 1, then extracted two times with 200 mL methylene chloride. The organic extracts were combined, washed with water (80 mL), dried ($MgSO_4$) and concentrated in vacuo to give a solid. Trituration with hexanes afforded 1.2 g (82%) of the title product as a white solid, mp 140–2° C. $^1$H-NMR ($d_6$-DMSO): δ 7.47 (m, 1H), 6.84 (m, 1H).

Anal. Calcd. for $C_5H_3O_2SF$: C, 41.10; H, 2.07. Found: C, 41.16; H, 1.98.

EXAMPLE 3

5-Fluoro-thiophene-2-carbonyl chloride

A mixture of the title compound of Example 2 (200 mg, 1.37 mmol), thionyl chloride (500 μl, 6.85 mmol) and DMF (20 μl) in dry methylene chloride was refluxed for 2 hours. The solvents were evaporated and the residue dried in vacuo to give 183 mg (81%) of the title product as a brown solid, mp 123–5 C. $^1$H-NMR ($CDCl_3$): δ 7.74 (m, 1H), 6.64 (m, 1H),). GC-MS (m/e, %) 166/164 ($M^+$, 11), 129(100).

We claim:

1. A process for the preparation of the compound of the formula

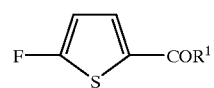

I wherein $R^1$ is OH, which comprises the steps of a) treating the compound of the formula

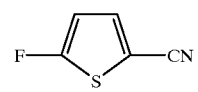

IV with an aqueous solution of a base, of the formula MOH, wherein M is an alkali metal cation and b) treating the product of step a) with a mineral acid.

2. The process according to claim 1 wherein step a) is effected at a temperature from about 20 to about 100° C.

3. The process according to claim 1 wherein M is selected from Li, Na and K, and said mineral acid is selected from HCl, $H_2SO_4$ and $H_3PO_4$.

4. The process according to claim 2 wherein M is Na, said mineral acid is HCl, and the reaction is effected at the reflux temperature of the NaOH solution.

5. The process according to claim 1 wherein the compound of formula IV is prepared by treating the compound of the formula

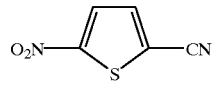

III with an inorganic fluoride, of the formula $M^2F$ wherein $M^2$ is an alkali metal cation, at an elevated temperature in the presence of a compound of the formula $(R^4)_4P^+$ $Z^-$ and a compound of the formula $R^5$vic $(COW)_2$ wherein $R^4$ and $R^5$ are each selected from optionally substituted $(C_6-C_{10})$aryl and optionally substituted $(C_1-C_6)$alkyl, and W is halo.

6. The process according to claim 5 wherein $M^2$ is selected from K, Rb or Cs, and $R^4$ is selected from phenyl and n-butyl, and Z is Cl or Br, and $R^5$ is phenyl, naphthyl or butyl, and W is Cl or F, and the solvent is selected from Sulfolane, DMSO, DMF and 1-methyl-2-pyrrolidinone, and the temperature is from about 140 to about 220° C.

7. The process according to claim 6 wherein $M^2$ is K, and $R^4$ and $R^5$ are each phenyl, and Z is Br, and W is Cl, and the solvent is Sulfolane and the temperature is about 180° C.

8. A process for the preparation of the compound of the formula

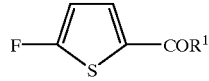

I wherein $R^1$ is OH, which comprises the steps of a) treating the compound of the formula

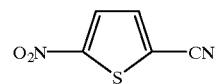

III with an inorganic fluoride, of the formula $M^2F$ wherein $M^2$ is an alkali metal cation, at an elevated temperature in the presence of a compound of the formula $(R^4)_4P^+$ $Z^-$ and a compound of the formula $R^5$vic $(COW)_2$ wherein $R^4$ and $R^5$ are each selected from optionally substituted $(C_6-C_{10})$aryl and optionally substituted $(C_1-C_6)$alkyl, and W is halo; to form the compound of the formula;

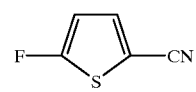

IV and b)
  i) treating the compound of the formula IV with an aqueous solution of a base, of the formula MOH, wherein M is an alkali metal cation and
  ii) treating the product of step i) with a mineral acid.

9. The process according to claim 8 wherein, in step a) $M^2$ is selected from K, Rb or Cs, and $R^4$ is selected from phenyl and n-butyl, and Z is Cl or Br, and $R^5$ is phenyl, naphthyl or butyl, and W is Cl or F, and the solvent is selected from Sulfolane, DMSO, DMF and 1-methyl-2-pyrrolidinone, and the temperature is from about 140 to about 220° C. and in step b) M is selected from Li, Na and K, and said mineral acid is selected from HCl, $H_2SO_4$ and $H_3PO_4$ and the temperature is from about 20 to about 100° C.

10. The process according to claim 9 wherein, in step a), $M^2$ is K, and $R^4$ and $R^5$ are each phenyl, and Z is Br, and W is Cl, and the solvent is Sulfolane and the temperature is about 180° C. and in step b) M is Na, said mineral acid is HCl, and the reaction is effected at the reflux temperature of the NaOH solution.

* * * * *